United States Patent [19]

Harris

[11] Patent Number: 5,422,282

[45] Date of Patent: Jun. 6, 1995

[54] METHODS FOR DETECTING AUTOIMMUNE SENSORINEURAL HEARING LOSS

[75] Inventor: Jeffrey P. Harris, La Jolla, Calif.

[73] Assignee: The Regents of the University of California, Oakland, Calif.

[21] Appl. No.: 116,042

[22] Filed: Sep. 1, 1993

Related U.S. Application Data

[63] Continuation of Ser. No. 692,633, Apr. 29, 1991, abandoned.

[51] Int. Cl.$^6$ .................................. G01N 33/564
[52] U.S. Cl. ............................ 436/506; 435/7.95; 435/975; 436/512; 436/518; 530/350; 530/387.1; 530/840
[58] Field of Search ............... 436/506, 501, 512, 518; 435/7.92, 7.93, 7.94, 7.95, 975; 530/350, 386, 387.1, 387.2, 840

[56] References Cited

U.S. PATENT DOCUMENTS 4,863,850 9/1989 Yamanaka et al. ............... 435/7.92

OTHER PUBLICATIONS

Arnold and Pfaltz, Critical Evaluation of the immunofluorescence microscope. Acta Otolaryngol. 103:373-378 (1987).

Arnold et al., Evidence of serum antibodies against inner ear tissues in the blood of patients with certain sensorineural hearing disorders. Acta Otolaryngol. 99:437-444 (1985).

Bowman and Nelson, HLA antigens in autoimmune sensorineural hearing loss. Laryngoscope 97:7-9 (1989).

Elles and Piester, Sensorineural hearing loss and immunity. In Veldman et al. (eds): Immunobiology, autoimmunity, transplantation in otorhinolaryngology, Berkeley, Calif. 1985, Kugler Publications.

Fisher and Hellistrom, Cogan's syndrome and systemic vascular disease. Arch. Pathol. 72:96-116 (1961).

Gussen R., Polyarteritis nodosa and deafness: a human temporal bone study. Arch. Otorhinolaryngol. 217:263-271 (1977).

Harris, J. P., Experimental autoimmune sensorineural hearing loss. Laryngoscope 97:63-76 (1987).

Haynes et al., Cogan's syndrome: studies in thirteen patients, long-term follow-up, and a review of the literature. Medicine 59(6):426-441 (1980).

Hughes et al., Autoimmune reactivity in Cogan's syndrome: A preliminary report. Otolaryngol. Head Neck Surg. 91:24-32 (1983).

Hughes et al., Autoimmune reactivity in Meniere's disease: a preliminary report. Laryngoscope 93:410-417 (1983).

Hughes et al., Predictive value of laboratory tests in autoimmune inner ear disease: preliminary report. Laryngoscope 96:502-505 (1986).

Jenkins et al., Polyarteritis nodosa as a cause of sudden deafness: a human temporal bone study. Am. J. Otolaryngol. 2:99-107 (1981).

Kanzaki and Ouchi, Steroid-responsive bilateral sensorineural hearing loss and immune complexes. Arch. Otorhinolaryngol. 230:5-9 (1981).

Leone et al., Endolymphatic sac: possible role in autoimmune sensorineural hearing loss. Ann. Otol. Rhinol. Laryngol. 93:208-209 (1984).

Luetje, C., Theoretical and practical implications for (List continued on next page.)

Primary Examiner—David Saunders
Attorney, Agent, or Firm—Campbell and Flores

[57] ABSTRACT

This invention provides a purified cochlear antigen reactive with an autoantibody associated with autoimmune sensorineuronal hearing loss. The purified antigen is defined as having a molecular weight of about 68,000 daltons as determined by SDS-PAGE analysis under reducing conditions. This invention also provides a method for detecting autoimmune sensorineural hearing loss in a patient. Finally, a kit containing reagents to assay for an antibody associated with autoimmune sensorineural hearing loss in a patient sample is disclosed and claimed by this invention.

14 Claims, No Drawings

OTHER PUBLICATIONS plasmapheresis in autoimmune inner ear disease. Plasmapheresis 99:1137–1146 (1989).

McAdam et al., Relapsing polychondritis: prospective study of 23 patients and a review of the literature. Medicine 55(3):193–214 (1976).

McCabe, B., Autoimmune sensorineural hearing loss. Ann. Otol. 88:585–589 (1979).

McCabe, B., Autoimmune inner ear disease: therapy. Am. J. Otol. 10(3):196–197 (1989).

Mosoloki, R., Western blot analysis of serum antibody to inner ear antigens in patients with idiopathic progressive bilateral sensorineural hearing loss (IPBSNHL). Am. Neurotology Society Meeting, Palm Beach, Fla. Apr. 27–29 (1990).

Orozco et al., Experimental model of immune-mediated hearing loss using cross-species immunization. Laryngoscope 100(9):941–947 (1990).

Schuknecht, H., Ear pathology in autoimmune disease. In: Pfaltz, C. R., Arnold, W., Kleinsasser, O. (eds.), Bearing of Basic Research on Clinical Otolaryngology. Basel: Karger, 1991, vol. 46, pp. 50–70.

Solliman, A. M., An improved technique for the study of immunofluorescence using non-decalcified frozen guinea pig cochlea. J. Laryngol. Otol. 102(3):215–218 (1986).

Soliman, A. M., Type II collagen-induced inner ear disease: critical evaluation of the guinea pig model. Am. J. Otol. 11(1):27–32 (1990).

Soliman and Zanetti, Improvements of a method for testing autoantibodies in sensorineural hearing loss. Ad. Oto-Rhino-Laryngology 39:13–17 (1988).

Veldman et al., Autoimmunity and inner ear disorders: an immune-complex mediated sensorineural hearing loss. Laryngoscope 94:501–507 (1984).

Yoo et al., Type II collagen autoimmunity in otosclerosis and Meniere's disease. Science 17:1153–1155 (1982).

Yoo et al., Type II collagen-induced autoimmune sensorineural hearing loss and vestibular dysfunction in rats. Ann. Otol. Rhinol. Laryngol. 92:267–271 (1983).

Zanetti et al. discuss whether in sera from patients with different forms of inner ear diseases antibodies against endoplasmic reticulum could be detected by ELISA in association with antisarcolemmal and antiendothelial antibodies (Progressive inner ear diseases . . . a consequence of secondary autoimmunity? HNO 35:34–37 (1987).

Autoimmune Sensorineural hearing loss: A preliminary experimental study Cruz et al; The Am Jo of Otology 11, #5, Sep. 1990, pp. 342–346.

Detection of Serum Antibody to inner ear antigens in patients with idiopathic progressive bilateral sensorineural hearing loss., R. Moscicki et al; Jo of Allergy Clin. Immunol. 85, #1, Jan. 1990, p. 149.

Inner Ear Autoantibodies in Patients with Rapidly Progressive Sensorineural Hearing Loss Harris J. P J Sharp P.A; Laryngoscope 100: May 1990 pp. 516–524.

Experimental Autoimmune Sensorineural Hearing Loss Harris, Laryngscope 97, Jan. 87, pp. 63–76.

METHODS FOR DETECTING AUTOIMMUNE SENSORINEURAL HEARING LOSS

This invention was made with Government support under Grant Nos. NS 18643 and NS 00606 awarded by the Department of Health and Human Services. The Government has certain rights in this invention.

This application is a continuation of application Ser. No. 07/692,633, filed Apr. 29, 1991, and now abandoned.

BACKGROUND OF THE INVENTION

The present invention relates generally to a biochemical assay for use in medical diagnosis and prognosis, and more specifically to an immunoassay for the diagnosis of autoimmune sensorineural hearing loss.

Autoimmune sensorineural hearing loss (ASNHL) is a disease characterized by progressive unilateral or bilateral deafness that, in its incipient stages, may fluctuate or become sudden and profound. Often disturbances of balance accompany the deafness. The pathogenesis of ASNHL and vestibular dysfunction is not well understood, but is presumed to include vasculitis of vessels supplying the inner ear, autoantibodies directed against inner ear antigenic epitopes or cross-reacting antibodies.

There are a number of disorders associated with hearing loss that have symptoms similar to autoimmune sensorineural hearing loss, thus making recognition of ASNHL difficult. The other disorders resulting in deafness include Meniere's disease, viral labyrinthitis, perilymph fistula, otosyphilis, and congenital or hereditary deafness. The determination of a specific etiology of the disease is of paramount importance with regard to determining appropriate therapeutic regimen.

Currently, no reliable test for autoimmune sensorineural hearing loss exists, although attempts have been made to develop one. Lymphocyte blastogenesis transformation assays against inner ear tissue and migration inhibition assays have been used, but both have low sensitivity. Immunofluorescence microscopy on animal or human temporal bones have also been used, but this procedure is technically difficult to perform because decalcification for sectioning alters antigenicity of the target tissue.

Thus, a need exists for a reliable test for autoimmune sensorineural hearing loss. Preferably, the test would be easy to perform and would be useful for predicting and monitoring a patient's response to immunosuppressive therapy. The present invention satisfies this need and provides related advantages as well.

SUMMARY OR THE INVENTION

The present invention relates to purified cochlear antigens reactive with autoantibodies associated with autoimmune sensorineural hearing loss. One cochlear antigen has a molecular weight in the range of about 62,000–68,000 daltons as determined by SDS-PAGE analysis under reducing conditions and at times appears as a double band. At other times, the antigen appears as a single band having a molecular weight of about 68,000 daltons and an isoelectric focusing point of about 6.3 by two dimensional gel electrophoresis. The present invention also relates to purified epitopes of such antigens having reactivity with the autoantibodies associated with autoimmune sensorineural hearing loss.

Purified polypeptides having specific reactivity with the cochlear antigens are also provided in the present invention. Such polypeptides can be antibodies or fragments thereof, and more particularly polyclonal or monoclonal antibodies.

The present invention is further directed to methods for detecting autoimmune sensorineural hearing loss in a patient and to prognostic methods for determining a patient's response to immunosuppressive therapy.

In a further aspect, the present invention relates to kits containing a polypeptide having specific reactivity with an autoantibody associated with autoimmune sensorineural hearing loss and ancillary reagents useful for performing the methods of the present invention. The polypeptide can be a cochlear antigen or an antibody.

DETAILED DESCRIPTION OF THE INVENTION

The present invention relates to the discovery of inner ear antigens, designated herein as "cochlear antigens," that are reactive with autoantibodies associated with autoimmune sensorineural hearing loss (ASNHL). The autoantibodies associated with ASNHL are found in the serum and inner ear fluid of humans and other animals whose inner ears express cochlear antigens.

Thus, one aspect of the present invention is directed to a purified cochlear antigen reactive with an autoantibody associated with ASNHL. One cochlear antigen has a molecular weight in the range of about 62,000–68,000 daltons as determined by SDS-PAGE analysis under reducing conditions and at times appears as a double band. At other times, the antigen appears as a single band having a molecular weight of about 68,000 daltons and an isoelectric focusing point of about 6.3 as determined by two dimensional gel electrophoresis. The antigen can be used as a diagnostic indicator of ASNHL.

A further cochlear antigen has been discovered having a molecular weight in the range of about 33,000–35,000 daltons, and more specifically about 34,000 daltons, as determined by SDS-PAGE analysis under reducing conditions. This antigen appears to be highly specific for inner ear tissue based on Western blot analysis. In these studies, sera from human patients suffering from ASNHL were analyzed for reactivity with various tissues, including inner ear, brain, liver and kidney. The 34,000 molecular weight (MW) antigen reacted strongly with the inner ear tissues, but not with the other tissues analyzed.

As noted previously, "cochlear antigens" refer to the inner ear antigens that are reactive with autoantibodies associated with ASNHL. Only a fragment of the primary structure of the cochlear antigens reactive with such autoantibodies may be required to effect antigenicity and are thus referred to as an "active fragment" of the antigen. A purified epitope specific or unique to a cochlear antigen is an example of an active fragment. The cochlear antigens and active fragments thereof are also within the meaning of the broad term "polypeptide," as used herein.

The term "active fragment" is also used in reference to other polypeptides of the present invention. Thus, an "active fragment" means a portion of an antigen or antibody of the present invention having substantially the desired binding region or binding affinity and specificity of the antigen or antibody, respectively. Such active fragments are included within the definition of the antigens and other polypeptides of the present invention for purposes of the disclosure herein.

As used herein, the term "purified" when used to describe a cochlear antigen or other polypeptides of the present invention, means the polypeptide is substantially free of other proteins or materials normally associated or occurring with such polypeptide in its native environment.

The cochlear antigens can be extracted from mammalian temporal bones, including human temporal bones, particularly human cadaveric temporal bones. Alternatively, the antigens can be extracted from surgical specimens taken at the time of acoustic tumor surgery or from fresh mammalian temporal bones. Although particularly useful bones are of human origin, other sources of temporal bones can also be obtained from other mammals, such as cows, guinea pigs, rats and the like. The membranous tissue can generally be extracted with appropriate solvents known in the art and the cochlear antigens isolated and purified by appropriate methods known in the art.

Purified cochlear antigens of the present invention can be used for a variety of purposes known in the art. For example, the purified antigens can be used to isolate and purify autoantibodies from the serum of patients with ASNHL. Methods of isolating and antibodies with antigens are well known in the art, including affinity purification. The purified autoantibodies can be used for various purposes, including the detection of cells and tissues expressing the cochlear antigens and for therapy.

The purified cochlear antigens of the present invention can also be used to raise either polyclonal or monoclonal antibodies by methods well known in the art. For example, methods for obtaining polyclonal antibodies are described in Harlow & Lane, *Antibodies: A Laboratory Manual*, 92–114 (Cold Springs Harbor Laboratory, 1988), which is incorporated herein by reference. Briefly, a solubilized cochlear antigen obtained from an animal source, particularly a human source, or an active fragment thereof, is injected into a host animal of another species, such as a rodent, rabbit, goat, sheep, pig and the like. The resulting antibodies are recovered from the serum and purified, if necessary, by means well known in the art, such as affinity purification for example.

Alternatively, monoclonal antibodies can be produced by means well known in the art such as those disclosed in Milstein & Kohler, *Nature* 256:495–497 (1975), incorporated herein by reference, or as modified by methods known in the art. A commonly employed process involves fusing, under appropriate conditions, an immortalizing cell line with a B-lymphocyte obtained from a host immunized with purified cochlear antigen or active fragment thereof. The fusion results in hybridomas that produce the desired antibody. The immortalizing cell line can be a murine myeloma line, although other lines can be used, such as a tumor line or cells obtained by transforming a normal cell line with, for example, an Epstein Barr virus.

Recombinantly produced antibody-like products are also within the definition of an "antibody" as used herein. Methods for producing such products are described, for example, in Skera & Pluckthun, *Science*, 240:1038–1040 (1988), which is incorporated herein by reference.

Thus, the present invention relates to purified polypeptides having specific reactivity with the cochlear antigens, including the antibodies described above. The polypeptides can be particularly useful for identifying tissues and cells that express a cochlear antigen.

The present invention further relates to purified polypeptides having specific reactivity with an autoantibody associated with autoimmune sensorineural hearing loss. Such polypeptides include, for example, idiotype antibodies having binding regions for the autoantibodies similar to the cochlear antigens of the present invention. Methods for producing idiotype antibodies are well known in the art. Alternatively, the polypeptide can be synthesized to mimic active fragments of the cochlear antigens according to methods well known in the art.

The availability of purified cochlear antigens with specific reactivity or binding affinity for the autoantibodies associated with ASNHL advantageously offers the possibility of a highly sensitive diagnostic assay for the hearing disorder. The present invention therefore further relates to methods for detecting autoimmune sensorineural hearing loss in a patient. Such methods include:

(a) contacting a sample from the patient with a detectable polypeptide specifically reactive with an autoantibody associated with autoimmune sensorial hearing loss; and (b) determining binding of the polypeptide to the sample, wherein polypeptide binding to the sample is indicative of autoimmune sensorineural hearing loss.

The term "patient," as used herein, means a human or other animal, such as a guinea pig, cow, rodent and the like, capable of having ASNHL, either naturally occurring or induced.

Various immunoassay methodologies are well known in the art and a vast literature now exists that describes various assay formats and modifications. All are based on the basic principle of determining the specific binding between ligands, such as an antigen and antibody. Such assays include competitive and noncompetitive formats, combined with homogeneous or heterogeneous formats. Generally, the antigen is immobilized on a solid support, which is then contacted with a sample of body fluid or tissue specimen. For the present invention, the sample is any fluid having or suspected of having autoantibodies associated with ASNHL. Such fluid samples can be serum, inner ear fluid and other bodily fluids containing cochlear antigens or a fluid sample containing an unknown quantity of such autoantibodies for use as a calibrator for example.

Various immunoprecipitation assays, including radioimmunoprecipitation, can be used. The well-known ELISA methods, which are described, for example, in R. Aloisi, *Principles of Immunology and Immunodiagnostics*, 152–176, 221–222 (1988) can also be used. Other useful immunoassay formats include sandwich assays as described in U.S. Pat. No. 4,376,110 and agglutination assays as described in U.S. Pat. No. 4,486,540. Particles, such as beads, or microparticles conjugated to or absorbed with antibodies or antigens, for instance, can be used in the sandwich assays as described, for example, in U.S. Pat. No. 4,879,215, all of which are incorporated herein by reference.

Western blotting assays can also be used and are particularly useful in the present invention due to their sensitivity. Briefly, inner ear extracts are electrophoresed on a polyacrylamide SDS gel and thereafter transferred to nitocellulose paper strips. The strips are incubated in diluted serum to be tested or other antibody-containing solution, followed by a secondary antibody. A radiolabeled ligand, such as iodine labeled staphylococcal protein A (SPA), can be added and developed on x-ray film.

In addition, conventional immunohistochemical staining techniques can also be used if tissues suspected of expressing the cochlear antigens wish to be analyzed. Such immunohistochemical methods are well known in the art. For example, immunoperoxidase staining procedures are described in Hsu et al., *J. Histochem. Cytochem.*, 29:577–580 (1981) as modified by Horan-Han et al., *Cancer Res.*, 43:728–735 (1983). Other assay formats known in the art can also be used to detect cochlear antigens.

The polypeptide binding to reactive components in a sample can be by any means known in the art, including the use of labels. For example, a labeled ligand reactive with a secondary antibody, particularly $^{125}$I-SPA, can be used as described previously. Alternatively, the polypeptide can be directly labeled with a detectable marker.

Such labels or markers include, for example, radioisotopes, enzymes, fluorogens, chromogens and chemiluminescent labels. For radioimmunoassays, suitable labels include tritium, carbon 14, phosphorous 32, iodine 125 or 131, yttrium-90, technetium-99 or sulfur 35. Examples of various suitable radioactive labels are described in U.S. Pat. No. 4,062,733.

Examples of various enzymatic markers include alkaline phosphatase, horseradish peroxidase, luciferase, beta-galactosidase, glucose oxidase, lysozyme, malate dehydrogenase and the like. Suitable substrates for the enzymatic systems include simple chromogens and fluorgens such as, for example, para-nitrophenyl phosphate, beta-D-glucose, homovanillic acid, o-dianisidine, bromocresol purple, 4-methyl-umbelliferone and indoxyl phosphate. Chromogenic labels are compounds that absorb light in the visible ultraviolet wavelengths. Such compounds are usually dyes. Fluorogenic compounds emit light in the ultraviolet or visible wavelength subsequent to irradiation by light or other energy source. A representative listing of suitable fluorogens are described in U.S. Pat. Nos. 4,366,241 and 3,996,345, both which are incorporated herein by reference. Chemiluminescent labels include, for example, those identified in U.S. Pat. No. 4,104,029.

Depending on the nature of the label or catalytic signal producing system used, a signal can be detected by means known in the art. For example, in the case of a radioactive label, a radiation counter can be used, such as a gamma counter for gamma-emitting markers. For fluorescent labels, a signal can be detected by irradiating with light and observing the level of fluorescence in a fluorometer. For enzyme-catalyzed systems, a color change can be detected visually for a positive reaction when a chromogenic label is used. Further quantification of an enzymatic reaction can be accomplished with a densitometric analysis. The comparison of reactivity both before and following treatment with immunosuppressive therapy and for monitoring purposes allows the practitioner to assess response to treatment.

In studies related to this invention, it was found that serum from 35% of patients with progressive sensorineural hearing loss tested positive for autoantibody specific for cochlear antigen. The antigen against which their serum reacted had the same molecular weight (62,000–68,000 daltons) and the same isoelectric point as found in the experimental ASNHL induced in guinea pigs. These results provide strong evidence that some patients with rapidly progressive sensorineural hearing loss have autoantibodies to a particular antigen within the inner ear and evidences an organ-specific autoimmune event. In a later study, 11 patients with the same autoantibody, as determined by Western blot analysis against their serum, showed improved hearing when given immunosuppressive therapy.

Subsequent studies in research related to the present invention have shown that of 138 patients with progressive sensorineural hearing loss, 46 patients were positive for ASNHL (33%) tested by Western blot analyses, which showed a positive band at about 68,000 daltons. Of these patients, 29 were female (63% of the positives) and 17 were male (37% of the positives). These results are consistent with findings in the art that females have a higher incidence of other autoimmune diseases.

Thus, the present invention in a further aspect provides methods for predicting the effectiveness of immunosuppressive therapy. In the methods of the present invention, the prognosis of a patient can be related to the binding of the detectable polypeptide to the sample in which polypeptide binding indicates a favorable prognosis of the patient to immunosuppressive therapy. A favorable prognosis means the patient will most likely respond to such therapy with improved hearing.

Relatedly, the methods of the present invention can be used to determine the appropriate treatment modality of a patient having a sensorineural hearing loss. If the assay is positive for autoantibodies to ASNHL, then immunosuppressive therapy is indicated. Without a confirmed diagnosis of autoimmune disease, many patients have undergone inappropriate immunosuppressive treatment or developed irreversible inner ear damage.

In addition, autoantibodies to the 68,000 dalton inner ear antigen have been found in children. The finding may be helpful in understanding the etiology of childhood hearing loss. Until recently, childhood hearing loss was considered a genetic disease or the result of unknown events such as febrile illness. In fact, evidence now suggests that autoantibodies to the 68,000 dalton inner ear antigen may play a role in these disorders.

In another aspect of the present invention, kits for performing the methods of the present invention are also provided. The kits can include any of the polypeptides reactive with an autoantibody associated with ASNHL and ancillary reagents. The polypeptide can be a cochlear antigen or antibody of the present invention. If required, the kit can contain a signal generating substance to provide or enhance detection. In addition, ancillary reagents can include, for example, stabilizers, buffers, controls, calibrators and the like that are known in the art.

The following examples are intended to illustrate, but not limit, the present invention.

EXAMPLE I

Antigen Preparation

Fresh bovine temporal bones were obtained from a local abattoir and were either used immediately or stored at −20° C. Temporal bones were obtained from cadavers of adult humans. The tissue from the bones was harvested by drilling open the temporal bone and the otic capsule. Utilizing an operating microscope, the membranous labyrinthine material was teased out of the inner ear and homogenized in iced phosphate buffered saline (PBS) containing 0.3% of the protease inhibitor, Trasylol (Behringer-Mannheim Biochemicals, Indianapolis, Ind.), 1% NP40 (Pierce Chem. Co., Rockford, Ill.), 0.5% sodium deoxycholate, and 0.1% SDS. The extract was sonicated for 1 minute on ice, centrifuged at 2500 rpm for 10 minutes, and sterile filtered through a 0.22 μm filter. A Folin determination as described in Lowry et al., *J. Biol. Chem.*, 193:265-2175 (1951) revealed that 0.2 mg to 0.5 mg of inner ear antigen could be harvested from a single temporal bone.

EXAMPLE II

Generation of ASNHL in Guinea Pigs

An experimental model of autoimmune sensorineural hearing loss was established by immunizing Hartley guinea pigs with an emulsion of 100 μg/0.2 ml of bovine inner ear antigen in complete Freund's adjuvant. The animals were boosted at three and eight weeks with 50 μg of bovine inner ear antigen in incomplete Freund's adjuvant. Between 1 and 4 weeks later, serum was taken for Western blot analysis, and the animals were vitally perfused with 5% phosphate-buffered paraformaldehyde as described in Harris, *Laryngoscope*, 97:63-76 (1987). The temporal bones were decalcified in phosphate buffered 10% disodium EDTA, pH 6.8, embedded in paraplast, and processed for hematoxylin and eosin staining.

The hearing of these animals was also tested electrophysiologically during the same time period. Of the animals tested, 32% showed significant sensorineural hearing loss compared to control animals. Cochlea sections from these animals had histological evidence of spiralganglion and neural degeneration with lymphocytic infiltrations. Furthermore, these animals all had high levels of antibody to inner ear antigen in their serum and inner ear fluid (perilymph). An immunoblot analysis (Western Blot) showed that an antibody from the hearing loss animals specifically reacted with the 68,000 dalton molecular weight antigen and that while the non-hearing loss immunized animals showed a similar antibody it was much less prominent. Normal, non-immunized animals had no antibody present in their serum. The animals with hearing loss are referred to herein as EASNHL animals.

A second group of guinea pigs was immunized with 100 μg of inner ear antigen (68,000 MW) that was eluted off a 5% to 17% SDS polyacrylamide gel and boosted 3 weeks later. Serum was taken for study in the Western blot analysis.

EXAMPLE III

Identification of Antibodies Associated with ASNHT,

The cochlear material (μg/0.5ml) extracted as described in Example II was boiled for 5 minutes with 0.5 ml of sample buffer containing 2-mercaptoethanol and loaded onto a 5-17% polyacrylamide SDS gel. Standard molecular weight markers were loaded onto the outside line. The gels were electrophoresed at 200 volts for four hours. The proteins were transferred from the gel to nitrocellulose for 1 hour at 100 v in a Hoeffer transfer chamber (Hoeffer Scientific Instruments, San Francisco, Calif.). The nitrocellulose was cut into strips and blocked with 5% nonfat milk in a standard phosphate buffered blotto solution for 5 minutes.

The strips were incubated overnight at 4° C. with serum samples from patients suspected of having autoimmune sensorineural hearing loss, from patients having no hearing loss and from a guinea pig with known autoimmune sensorineural hearing loss experimentally induced as in Example I. Excess antibody was washed away with 1.0% Triton X in PBS. The strips were reblocked with blotto. Anti-IgG antibodies were obtained by immunizing a rabbit with either human IgG for use with human samples or guinea pig IgG for use with guinea pig samples. The resulting anti-serum was collected and purified by ammonium sulfate precipitation and dialyzing against saline according to standard procedures known in the art.

The secondary antibody was added to the strips at 1:500 dilution (Rabbit anti-human IgG for humans samples and rabbit anti-guinea pig IgG for guinea pig samples) for 1 hour at room temperature with gentle rocking. The strips were then washed and reblocked with blotto. $^{125}$I-SPA (Staphylococcal-protein A) radiolabeled at $1 \times 10^6$ cpm/ml was added for 1 hour at room temperature. The strips were washed, rinsed in distilled water, dried, and laid out on Kodak XRP x-ray film.

A labeled band was evident in the lane containing the patient sample which corresponded to a similar labeled band seen in the lane containing the guinea pig sample. The migration of the band corresponded to a molecular weight of approximately 68,000.

EXAMPLE IV

Two-Dimensional Gel Analysis

Antibodies having similar specificity against cochlear antigens were identified in the sera of guinea pigs and human patients suspected of suffering from autoimmune sensorineural hearing loss. To determine whether the antigens reactive with these antibodies are identical, two dimensional gel electrophoresis was performed.

The serum of a patient with hearing loss, identified as case 1 in Example VII below, was compared with the sera of no hearing loss guinea pigs and control sera. The sera were incubated with bovine cochlear antigen extracts labeled with $^{125}$I ($5 \times 10^6$ cpm) for 30 minutes at 4° C. and precipitated with 25 μl of Protein-A-Sepharose (Pharmacia). The immunoprecipitates were washed in Tris Buffered Saline (TBS) plus 1% NP40, microfuged, layered on 20% sucrose in TBS then microfuged and stored at −70° C.

Two-dimensional gel electrophoresis was performed using the immunoprecipitates. Thirty-five microliters of sample buffer containing 2-β-mercaptoethanol (2-ME) was added to the pellets for one hour at 25° C. To determine the isoelectric point (pI), the immunoprecipitates were microfuged, counted in a gamma counter, and equivalent counts from the supernatant were layered onto individual gels containing ampholytes pH 3.5 to 9. Before loading the immunoprecipitates, the gels were prefocused for one hour by starting at 200V. The voltage was increased in increments of 100V every 10 minutes until 1000V was reached. After equivalent counts of the immunoprecipitates were layered onto the individual gels, the loaded gels were focused for 8-10 hours at 1000V. The gels were then removed from the tubes and frozen at −70° C.

To determine the molecular weight of the antigens, the gels were thawed and 1 ml of TBS buffer with 2-ME was added to the gels for 10-20 minutes. The gels were then placed on top of a 14 cm, 7.5% SDS-polyacrylamide slab gel and electrophoresed for 5 hours at 30 mA. The gel was fixed in 10% acetic acid, 10% propanol for 10-20 minutes, then transferred to Whatman #3 filter paper, and dried in a BioRad Slab gel dryer. The dried gels were exposed to Kodak XAR-2 film with intensifying screens for 2 days at −70° C. Molecular weight markers were electrophoresed in the slab gels and an isoelectric focused gel was eluted for the isoelectric focusing point determination. The blots that appeared on the film were then analyzed for their isoelectric focusing point and molecular weight. The molecular weight was determined to be about 68,000 daltons, while the pI was about 6.3.

The results of the analysis demonstrate that sera of EASNHL guinea pigs and sera of humans with deafness contain identical proteins, both having a molecular weight of about 68,000 daltons and an isoelectric point of about 6.3. Thus, the results indicate that an autoimmune etiology results in hearing loss in some patients. These results provide compelling evidence that the antigenic epitopes against which both the EASNHL animals and the human patient sera react are the same, since it would be exceedingly rare that two substances share the same molecular weight and isoelectric point. Consequently, the results indicate that hearing loss in certain patients has an autoimmune etiology.

EXAMPLE V

Western Blot Analysis

For each Western blot analysis, 750 µg of inner ear extract were used in the assay described in Example III. Serum was collected from human patients and run against fresh preparations of inner ear antigen obtained from the temporal bones of human cadavers, guinea pigs or cows.

The human patient population consisted of individuals with idiopathic progressive sensorineural hearing loss (N=54). Nineteen (35%) showed evidence of a single- or double-band migrating at about 62,000–68,000 molecular weight. This result differed significantly from the normal population (N=14) in which one (7%) showed a similar band (P=0.031 Fisher's exact test).

Since serum contains cross-reacting antibodies or proteins that might produce banding that is not relevant, serum from EASNHL animals that had become deafened was used as a control. The immunized animals were divided into two groups and their serum was pooled based on the presence or absence of hearing loss. The immunized animals with hearing loss showed heavy banding at 68,000 molecular weight, whereas the immunized animals with normal hearing showed much less reactivity at that molecular weight. Normal nonimmunized guinea pigs had no reactivity against bovine inner ear antigen. The locations of the bands in the case histories of Example VII were identical to those seen in the EASNHL animals.

Discrete labeling was seen at about 62,000–68,000 molecular weight in autoimmune sensorineural hearing loss patients compared to that observed for a control patient without hearing loss and for a patient with sensorineural hearing loss of other causes.

Patients with other autoimmune conditions such as ulcerative colitis show variable reactions. Since two of the patients with a positive immunoblot also had inflammatory bowel disease, sera from three additional patients with ulcerative colitis, but without hearing loss, were also tested. Of these, two samples were positive and one was negative. Patients with ulcerative colitis are believed to have a predilection for the development of sensorineural hearing loss. Thus, the presence of a positive immunoblot in these two patients with normal hearing could be used as a prognostic indicator of autoimmune sensorineural hearing loss.

EXAMPLE VI

Double Precipitation Assay

A double precipitation assay can be equally effective for the diagnosis of autoimmune sensorineural hearing loss. The assay uses the 68,000 dalton purified cochlear antigen. The cochlear antigen is iodinated with $I^{125}$ according to standard techniques. To triplicate wells, $I^{125}$ labeled antigen is incubated with 5 ml of serum from autoimmune sensorineural hearing loss patients or control serum. Triplicate wells containing $^{125}I$ aliquots alone to which 5 ml of serum sample is added serve as a control. After overnight incubation at 4° C., goat anti-human gamma globulin (15% $Na_2SO_4$ cut) is added. The amount of goat antibody added is that which gives the maximum precipitate when tested with 5 ml of normal human serum. After 4 hour incubation at 4° C. the tubes are centrifuged and the pellets washed once and the radioactivity of the pellet determined. The radioactivity of the non-antigen $I^{125}$ blanks are subtracted from the average radioactivity values from the wells containing cochlear antigen $I^{125}$ and a titer determined.

EXAMPLE VII

Case Histories

Case 1

An 11-year-old boy (R.M.) was in excellent health until 6 months prior to presentation, when he developed intermittent episodes of true vertigo with nausea and vomiting lasting seconds to hours. There was no associated hearing loss at that time. Approximately 4 months later, he noted gradually progressive and fluctuating left-sided hearing loss with subsequent involvement of his right ear as well.

Evaluation included a normal BERA and CT scan of the brain and posterior fossa. Complete blood count (CBC) was normal and erythrocyte sedimentation rate (ESR) was slightly elevated at 20 mm/hr (normal range 1–10 mm/hr). An audiogram showed bilateral sensorineural hearing loss with a speech reception threshold (SRT) of 55 dB AS, 80 dB AD, and speech discrimination score of 92% AS and 32% AD.

A trial of prednisone 40 mg q.d. was begun and a gradual improvement in hearing in both ears was noted over a 4-week period. Attempts to taper the prednisone to 15 mg q.d. were associated with a drop in hearing; thus, he was maintained on 40 mg of prednisone on an alternate-day basis. Hearing continued to fluctuate when steroids were tapered, but improved on high-dose maintenance.

Further laboratory testing revealed normal immunoglobulin levels (IgA 170 mg/dL; IgG 1060 mg/dL; IgM 126 mg/dL), ClQ binding 108% (normal range 40–150), Raji cell assay 98 mcg aggregated human gammaglobulin (AHG) EQ/ml (elevated >100), ANA positive speckled at 1:16 titer, negative rheumatoid factor, normal thyroid function tests, negative FTA-ABS, and a normal urinalysis.

Immunoblot was performed with the patient's serum against inner ear antigen and two labeled bands that migrated between 62,000–68,000 MW were observed.

Case 2

A 36-year-old woman developed sudden onset of vertigo followed 5 days later by hearing loss and tinnitus in her right ear. A short course of steroids restored her hearing until 4 months later when, because of daily fluctuations in her AD hearing, a surgical exploration of the right ear was performed to rule out a perilymph fistula. Two days after surgery, she developed sudden left-sided hearing loss followed shortly thereafter by ataxia.

Medical history included nonrheumatic migratory arthritis, and a 12-year history of ulcerative colitis (ULC) that was well controlled on Azulfidine$^R$ Upon admission to the hospital, laboratory evaluation revealed: hemoglobin 6.3, hematocrit 22%, platelet count 67,000, ESR 27 mm/hr, negative FTA-ABS, positive rheumatoid factor (1:32), positive ANA (>1:640), normal quantitative immunoglobulins (IgA, IgM, IgG), positive Raji cell assay, positive anti-platelet antibody, negative anti-cardiolipin, negative anti-DNA, negative anti-histone, negative anti-RPR, negative lupus-anticoagulant. Audiogram showed a severe sensorineural hearing loss (SRT 85 dB) with poor speech discrimination (12%) AS and a low- and high-frequency sensorineural hearing loss AD.

Further evaluation included: normal MRI, absent BERA wave forms AS, delayed waves I-V, AD. Visual evoked responses (VER) were normal, lymphocyte transformation was negative against inner ear antigen with good PHA responses (SI of 54). Immunoblot of her serum against inner ear antigen revealed a labeled band migrating at the same molecular weight as the patient in case 1.

The patient underwent treatment with high dose prednisone 60 mg/day, cytoxan 260 mg tapered to 100 mg/day and lymphoplasmapheresis. The ataxia cleared and hearing greatly improved. Post-treatment immunoblots of her serum showed greatly reduced reactivity against inner ear antigen. After 1 year of treatment, she is off all medication, although hearing continues to fluctuate.

Case 3

A 69-year-old man developed an upper respiratory infection with associated bilateral serous otitis media and dizziness. He was treated conservatively, and 1 month later became profoundly deafened bilaterally, ataxic, and confused. He was admitted to the neurology service to rule out a cerebrovascular accident.

Medical history included mild adult-onset diabetes mellitus (AODM) and inflammatory bowel disease. During evaluation, an audiogram revealed a severe to profound sensorineural hearing loss bilaterally with 0% speech discrimination. Laboratory findings included: ESR 60 mm/hr, ANA negative, negative rheumatoid factor, quantitative immunoglobulins elevated IgM, but normal IgA and IgG, and negative FTA-ABS. Antibodies to herpes simplex and Epstein-Barr virus (EBV) were negative. An electronystagmogram showed absent caloric responses bilaterally, a cerebral angiogram showed no evidence of arteritis, and a CT scan was normal. Lymphocyte transformation to inner ear antigen was negative with good PHA responses.

He was placed on prednisone 60 mg/day and had excellent return of hearing AD, but only minimal recovery AS. Steroids were tapered over 5 months to 10 mg/day when the patient developed increasing tinnitus AD. Due to AODM the steroids were subsequently stopped, and 1 week later he had a profound drop in hearing bilaterally. The prednisone was restarted and he recovered partial hearing in his right ear only. The patient subsequently died of presumed myocardial infarction. An autopsy was not performed. Analysis of his serum and cerebrospinal fluid (CSF) kept at −70° C. against inner ear antigen by immunoblot showed a labeled band in the serum only, which migrated at the identical molecular weight as seen in cases 1 and 2.

EXAMPLE VIII

Observation of a 34,000 MW Antigen

In additional studies, tissues from bovine temporal bone were subjected to a more complex extraction method before a Western blot analysis was performed. The tissues were first homogenized in an aqueous 10 mM Tris buffer solution (pH 6.8), Trasylol (2 μg/ml) and centrifuged at 100,000 ×g for 1 hour. The pellet was again homogenized with 0.5% SDS, 50 mM Tris buffer (pH 6.8), 2 mM PMSF, 4 mM EDTA, 10 mM NEM. The homogenate was centrifuged at 10,000 ×g for 10 minutes. The supernatant was used as the source of inner ear antigen.

The Western blot analysis with sera of patients with ASNHL resulted in the observation of another cochlear antigen of about 34,000 daltons. The 34,000 dalton cochlear antigen appeared to be in higher concentration than the 62,000–68,000 doublet and appeared to be more specific to the inner ear tissues. No reactivity was observed at 34,000 MW with kidney, liver or brain tissues. Some reactivity was observed at the 68,000 MW with kidney, liver and brain tissues.

One patient serum was pre-treated with BSA to block anti-BSA antibodies in the serum. Reactivity patterns were similar to other patient serum without pre-treatment with BSA.

EXAMPLE IX

Lymphocyte Transformation Assay

For comparison purposes, a lymphocyte transformation assay was conducted. Separation of peripheral blood lymphocytes (PBLs) was accomplished by a ficoll-hypaque discontinuous density gradient. Blood from patients and controls (20 ml) was collected in 0.2 ml of heparin. The anticoaggulated blood was diluted 1:3 in Hanks balanced salt solution containing 5 mM EDTA. One volume of ficoll-hypaque was layered under three volumes of diluted blood and centrifuged at 1200 rpm for 40 minutes. The interface containing the PBLs was removed, suspended in Hanks balanced salts, and centrifuged at 600 rpm for 8 minutes to remove platelets.

The PBLs were resuspended in 10 cc of RPMI 1640 containing 10% fetal bovine serum (FBS) and incubated for 1 hour at 37° C. and 5% $CO_2$ in a 100 mm tissue culture dish with occasional shaking. The unattached cells were collected, spun at 100 rpm for 10 minutes in RPMI and suspended in RPMI 1640 containing 20% FBS and 100 μg/ml gentamicin. The nucleated cells were counted and adjusted to $3 \times 10^6$/ml.

One hundred microliters of cells were added to triplicate wells of a 96-well, flat-bottomed microtitre plate. One hundred microliters of phytohemagglutinin (PHA) (2 μg/ml), 100 μl of human inner ear extract (40 μg/ml or 500 ng/ml), 100 μl human skin extract (40 μg/ml or 500 ng/ml), or RPMI were added to the cultures. PHA cultures were pulsed on day 2 with 10 μl (0.4 μCi) of tritiated thymidine for 18 hours. Antigen cultures were pulsed on day 5. Plates were harvested on fiber disks and counted in 5 ml of scintifluor. Stimulation indices (SI) were calculated by dividing the mean counts per minute of the stimulated cultures by the mean cpm of unstimulated cultures.

Table I shows the results of lymphocyte transformation in 26 patients with progressive sensorineural hearing loss and 19 controls.

TABLE I

| Group | PHA | IE | Skin |
|---|---|---|---|
| Control (N = 19) | 42 ± 32 | 0.77 ± 0.27 | 1.1 ± 0.38 |
| Patient (N = 26) | 44 ± 29 | 0.80 ± 0.27 | 1.2 ± 0.43 |

Despite excellent PHA responses in both groups, no significant SI difference was demonstrated upon exposure to human inner ear antigen (IE) versus preparations from human skin (Skin).

The foregoing description of the invention is exemplary for purposes of illustration and explanation. It will be apparent to those skilled in the art that changes and modifications are possible without departing from the spirit and scope of the invention. It is intended that the following claims be interpreted to embrace all such changes and modifications.

I claim:

1. A purified cochlear antigen reactive with an antibody associated with the presence of autoimmune sensorineural hearing loss in a patient, the antigen having a molecular weight of about 68,000 daltons as determined by SDS-PAGE under reducing conditions and an isoelectric point of about 6.3.

2. A purified polypeptide, wherein the polypeptide is an antibody specifically reactive with the antigen of claim 1, or a fragment of the antibody, the fragment also being specifically reactive with the antigen of claim 1.

3. The purified cochlear antigen of claim 1 labeled with a detectable marker.

4. The purified polypeptide of claim 2, labeled with a detectable marker.

5. A method for detecting an antibody associated with the presence of autoimmune sensorineural hearing loss in a patient, comprising:
   a. obtaining a suitable sample from the patient;
   b. contacting the sample with the purified antigen of claim 1 under conditions favoring the formation of antibody-antigen complex;
   c. detecting the presence of any complex;
   d. the presence of complex being a positive detection of the antibody associated with the presence of autoimmune sensorineural hearing loss in the patient.

6. The method of claim 5, wherein the antigen is labeled with a detectable marker.

7. The method of claim 5, wherein step b further comprises contacting the sample with a labeled ligand, the ligand being specifically reactive with antibody in the sample.

8. A method for diagnosing autoimmune sensorineural hearing loss in a patient suspected of having autoimmune sensorineural hearing loss, comprising:
   a. obtaining a suitable sample from the patient;
   b. contacting the sample with the purified antigen of claim 1 under conditions favoring the formation of antibody-antigen complex;
   c. detecting the presence of any complex;
   d. the presence of complex being a positive diagnosis that the patient has autoimmune sensorineural hearing loss.

9. The method of claim 8, wherein the antigen is labeled with a detectable marker.

10. The method of claim 8, wherein step b further comprises contacting the sample with a labeled ligand, the ligand being specifically reactive with antibody in the sample.

11. A method for monitoring immunosuppressive therapy in a patient having autoimmune sensorineural hearing loss, comprising:
    a. obtaining a suitable sample from the patient;
    b. contacting the sample with the purified antigen of claim 1 under conditions favoring the formation of antibody-antigen complex;
    c. detecting and quantifying the presence of any complex;
    d. repeating steps a. through c. subsequent to the patient receiving the immunosuppressive therapy; and
    e. comparing the quantification of detected complex prior to and subsequent to the patient receiving immunosuppressive therapy.

12. The method of claim 11, wherein the antigen is labeled with a detectable marker.

13. The method of claim 11, wherein step b further comprises contacting the sample with a labeled ligand, the ligand being specifically reactive with antibody in the sample.

14. A kit for detecting antibodies comprising ancillary reagents and the purified cochlear antigen of claim 1.

* * * * *

UNITED STATES PATENT AND TRADEMARK OFFICE
CERTIFICATE OF CORRECTION

PATENT NO. : 5,422,282
DATED : June 6, 1995
INVENTOR(S) : Jeffrey P. Harris

It is certified that error appears in the above-indentified patent and that said Letters Patent is hereby corrected as shown below:

In column 1, line 54, please delete "SUMMARY OR THE INVENTION" and replace therefor with --SUMMARY OF THE INVENTION--.

Signed and Sealed this

Fourteenth Day of November, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,422,282
DATED : June 6, 1995
INVENTOR(S) : Jeffrey P. Harris

It is certified that error appears in the above-indentified patent and that said Letters Patent is hereby corrected as shown below:

In column 7, line 50, please delete "ASNHT," and replace therefor with --ASNHL,--.

Signed and Sealed this

Fourth Day of June, 1996

BRUCE LEHMAN

Attest:

Attesting Officer

Commissioner of Patents and Trademarks